US011315056B2

(12) United States Patent
Almashor et al.

(10) Patent No.: US 11,315,056 B2
(45) Date of Patent: Apr. 26, 2022

(54) RESOURCE PLANNING HAVING IMPROVED VISUALIZATION

(71) Applicant: INTERNATIONAL BUSINESS MACHINES CORPORATION, Armonk, NY (US)

(72) Inventors: Mahathir Bin Ahmad Almashor, Airport West (AU); Hamideh Anjomshoa, Camberwell (AU); Adam Eberbach, Surrey Hills (AU); Olivia Jayne Smith, Parkville (AU); Annalisa Jean Swan, Brunswick East (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 189 days.

(21) Appl. No.: 16/376,128

(22) Filed: Apr. 5, 2019

(65) Prior Publication Data

US 2020/0320454 A1 Oct. 8, 2020

(51) Int. Cl.
*G06Q 10/06* (2012.01)
*G06Q 10/04* (2012.01)
*G16H 40/20* (2018.01)

(52) U.S. Cl.
CPC ....... *G06Q 10/06315* (2013.01); *G06Q 10/04* (2013.01); *G16H 40/20* (2018.01)

(58) Field of Classification Search
CPC .............................................. G06Q 10/06315
See application file for complete search history.

(56) References Cited

U.S. PATENT DOCUMENTS

| 7,305,348 B1 | 12/2007 | Brown |
| 7,555,436 B2 | 6/2009 | Brown |
| (Continued) | | |

FOREIGN PATENT DOCUMENTS

| CA | 2945131 A1 * | 10/2015 | ............. G06Q 10/06 |
| CA | 2932758 A1 * | 12/2016 | ............. G06F 19/00 |
| WO | 2009009686 A2 | 1/2009 | |

OTHER PUBLICATIONS

Sherif Sakr and Amal Elgammal, Towards a Comprehensive Data Analytics Framework for Smart Healthcare Services, Jun. 2016, Big Data Research.*

(Continued)

*Primary Examiner* — Jerry O'Connor
*Assistant Examiner* — Philip N Warner
(74) *Attorney, Agent, or Firm* — Cantor Colburn LLP; Joseph Petrokaitis

(57) ABSTRACT

Methods, systems and computer program products for providing an interactive resource plan visualization associated with a facility are provided. Aspects include receiving facility data comprising historical facility data, current facility data and demand data. Aspects also include determining projected resource demand based on the facility data and the demand data and using cognitive computing techniques. Aspects also include generating a visual representation of a facility. The visual representation of the facility includes available resources and resource demand associated with a specified time and the available resources are rendered according to a first visual style. Aspects also include determining resource availability modifications based on the available resources and the projected resource demand. Aspects also include generating a visual representation of the resource availability modifications associated with the specified time within the visual representation of the facility.

(Continued)

The resource availability modifications are rendered according to a second visual style.

19 Claims, 7 Drawing Sheets

(56) References Cited

U.S. PATENT DOCUMENTS

| | | | |
|---|---|---|---|
| 8,019,618 B2 | 7/2011 | Brown | |
| 8,005,690 B2 | 8/2011 | Brown | |
| 8,521,546 B2 | 8/2013 | Brown | |
| 2009/0018882 A1* | 1/2009 | Burton | G06Q 10/10 705/7.27 |
| 2011/0054946 A1* | 3/2011 | Coulter | G16H 30/20 705/2 |
| 2012/0065987 A1* | 3/2012 | Farooq | G16H 40/20 705/2 |
| 2012/0182245 A1* | 7/2012 | Hutton | G06Q 10/00 345/173 |
| 2012/0190386 A1* | 7/2012 | Anderson | H04L 67/306 455/456.3 |
| 2012/0232926 A1* | 9/2012 | Boyle | G16H 40/20 705/3 |
| 2012/0249797 A1* | 10/2012 | Haddick | G04G 21/04 701/491 |
| 2013/0093829 A1* | 4/2013 | Rosenblatt | H04N 7/18 434/365 |
| 2013/0262357 A1 | 10/2013 | Amarasingham et al. | |
| 2015/0095056 A1 | 4/2015 | Ryan et al. | |
| 2015/0339570 A1* | 11/2015 | Scheffler | G06N 3/10 706/27 |
| 2016/0350499 A1 | 12/2016 | Anjomshoa et al. | |
| 2017/0039765 A1* | 2/2017 | Zhou | G06T 7/521 |
| 2017/0185721 A1* | 6/2017 | Schuck | G16H 40/20 |
| 2018/0204172 A1* | 7/2018 | Sabuz | G06Q 10/0835 |
| 2019/0094981 A1* | 3/2019 | Bradski | G06F 3/017 |
| 2019/0189259 A1* | 6/2019 | Clark | G16H 10/60 |
| 2019/0201104 A1* | 7/2019 | Shelton, IV | A61B 1/00011 |
| 2019/0214116 A1* | 7/2019 | Eberting | G16H 80/00 |
| 2020/0027096 A1* | 1/2020 | Cooner | G06Q 20/308 |
| 2020/0105064 A1* | 4/2020 | Gulersen | G02B 27/017 |
| 2021/0052757 A1* | 2/2021 | Baarman | A61L 2/24 |
| 2021/0124465 A1* | 4/2021 | Sahu | G06F 3/0482 |
| 2021/0193302 A1* | 6/2021 | Day | G16H 40/20 |
| 2022/0035342 A1* | 2/2022 | Cella | G05B 19/4155 |

OTHER PUBLICATIONS

Creemers et al., "Modeling a Hospital Queueing Network," Queueing Networks, 2011, pp. 1-42.

Gartner et al., "Machine Learning Approaches for Early DRG Classification and Resource Allocation," INFORMS Journal on Computing 27 (4), Manuscript No. doi.org/10.1287/ijoc.2015.0655, Mar. 2015, pp. 1-35.

Ghaseem-Aghaee et al., "Simulation and Agents: Exploring the Synergy," AIN Intelligent Computational Systems: a Multidisciplinary Perspective, 2017, pp. 1-43.

Sibbel et al., "Agent-Based Modeling and Simulation for Hospital Management," Cooperative Agents, Springer Netherlands, 2001, 18 pages.

* cited by examiner

RESOURCE PLANNING HAVING IMPROVED VISUALIZATION

BACKGROUND

The present invention generally relates to programmable computing systems, and more specifically, to computing systems, computer-implemented methods, and computer program products configured to utilize cognitive computing techniques to analyze facility data and generate a resource plan for the facility that can be easily visualized.

Resource planning for a facility, such as a hospital, is typically performed by analyzing data representative of historical demand in view of facility resources to identify bottlenecks, inefficiencies, and other shortcomings in the process flow or optimization of the use of facility resources. Predictions and suggestions for modifications to resources can be made based on such analyses.

SUMMARY

Embodiments of the present invention are directed to a computer-implemented method for providing an interactive resource plan visualization associated with a facility. A non-limiting example of the computer-implemented method includes receiving, by a processor, facility data comprising historical facility data and current facility data. The method also includes receiving demand data. The method also includes determining projected resource demand based on the facility data and the demand data using cognitive computing techniques. The method also includes generating a visual representation of a facility. The visual representation of the facility includes available resources and resource demand associated with a specified time. The available resources are rendered according to a first visual style. The method also includes determining resource availability modifications based on the available resources and the projected resource demand. The method also includes generating a visual representation of the resource availability modifications associated with the specified time within the visual representation of the facility. The resource availability modifications are rendered according to a second visual style.

Embodiments of the present invention are directed to a system for providing an interactive resource plan visualization associated with a facility. The system includes a memory having computer readable computer instructions, and a processor for executing the computer readable instructions. The computer readable instructions include instructions for receiving facility data comprising historical facility data and current facility data. The computer readable instructions also include instructions for receiving demand data. The computer readable instructions also include instructions for determining projected resource demand based on the facility data and the demand data using cognitive computing techniques. The computer readable instructions also include instructions for generating a visual representation of a facility. The visual representation of the facility includes available resources and resource demand associated with a specified time. The available resources are rendered according to a first visual style. The computer readable instructions also include instructions for determining resource availability modifications based on the available resources and the projected resource demand. The computer readable instructions also include instructions for generating a visual representation of the resource availability modifications associated with the specified time within the visual representation of the facility. The resource availability modifications are rendered according to a second visual style.

Embodiments of the invention are directed to a computer program product for providing an interactive resource plan visualization associated with a facility, the computer program product comprising a computer readable storage medium having program instructions embodied therewith. The program instructions are executable by a processor to cause the processor to perform a method. A non-limiting example of the method includes receiving facility data comprising historical facility data and current facility data. The method also includes receiving demand data. The method also includes determining projected resource demand based on the facility data and demand data based on the facility data and the demand data using cognitive computing techniques. The method also includes generating a visual representation of a facility. The visual representation of the facility includes available resources and resource demand associated with a specified time. The available resources are rendered according to a first visual style. The method also includes determining resource availability modifications based on the available resources and the projected resource demand. The method also includes generating a visual representation of the resource availability modifications associated with the specified time within the visual representation of the facility. The resource availability modifications are rendered according to a second visual style.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
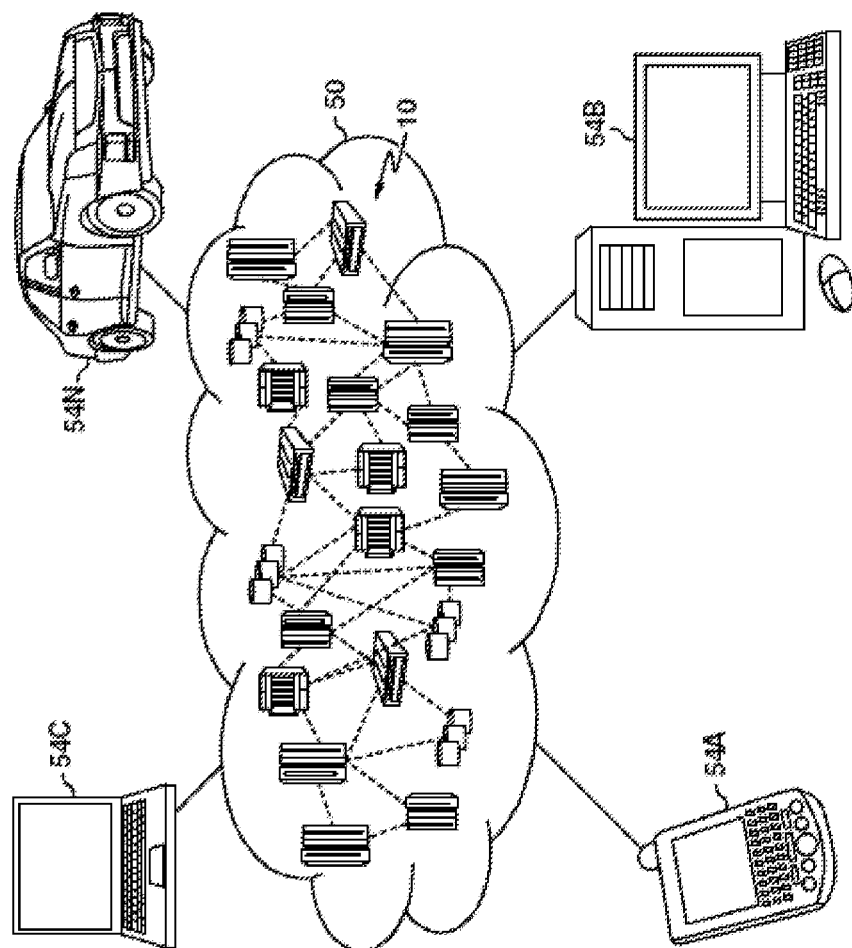
FIG. 1 depicts a cloud computing environment according to one or more embodiments of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
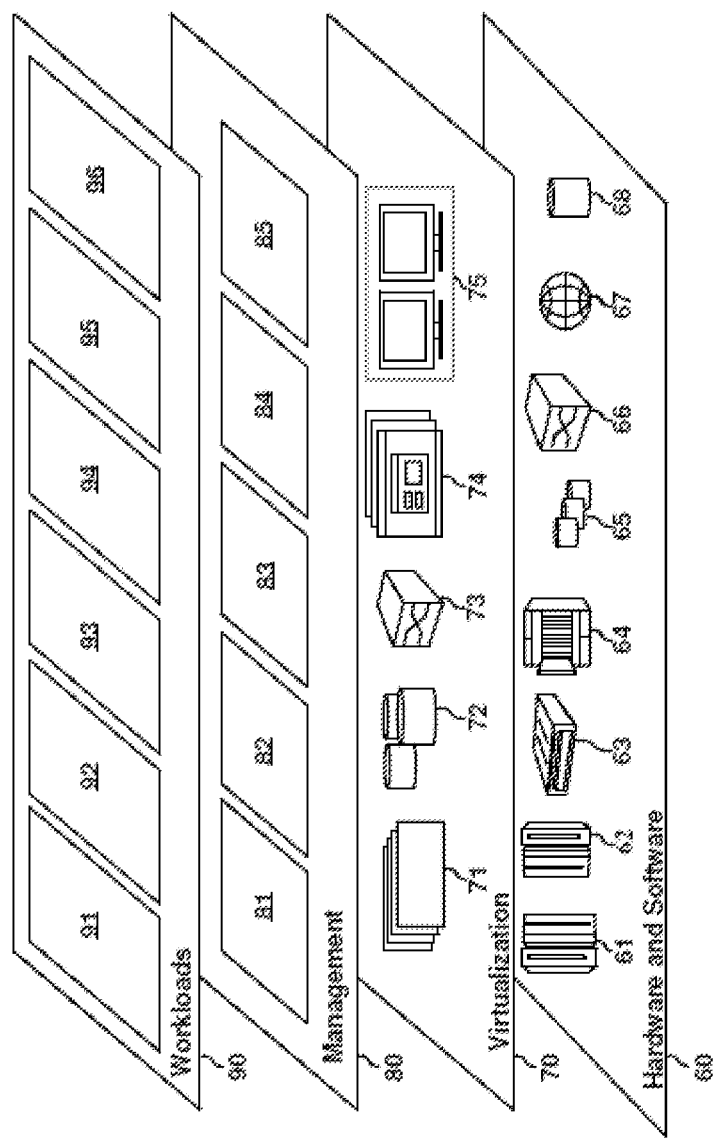
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments of the invention, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and providing an interactive resource plan visualization associated with a facility 96.

Figure 3:
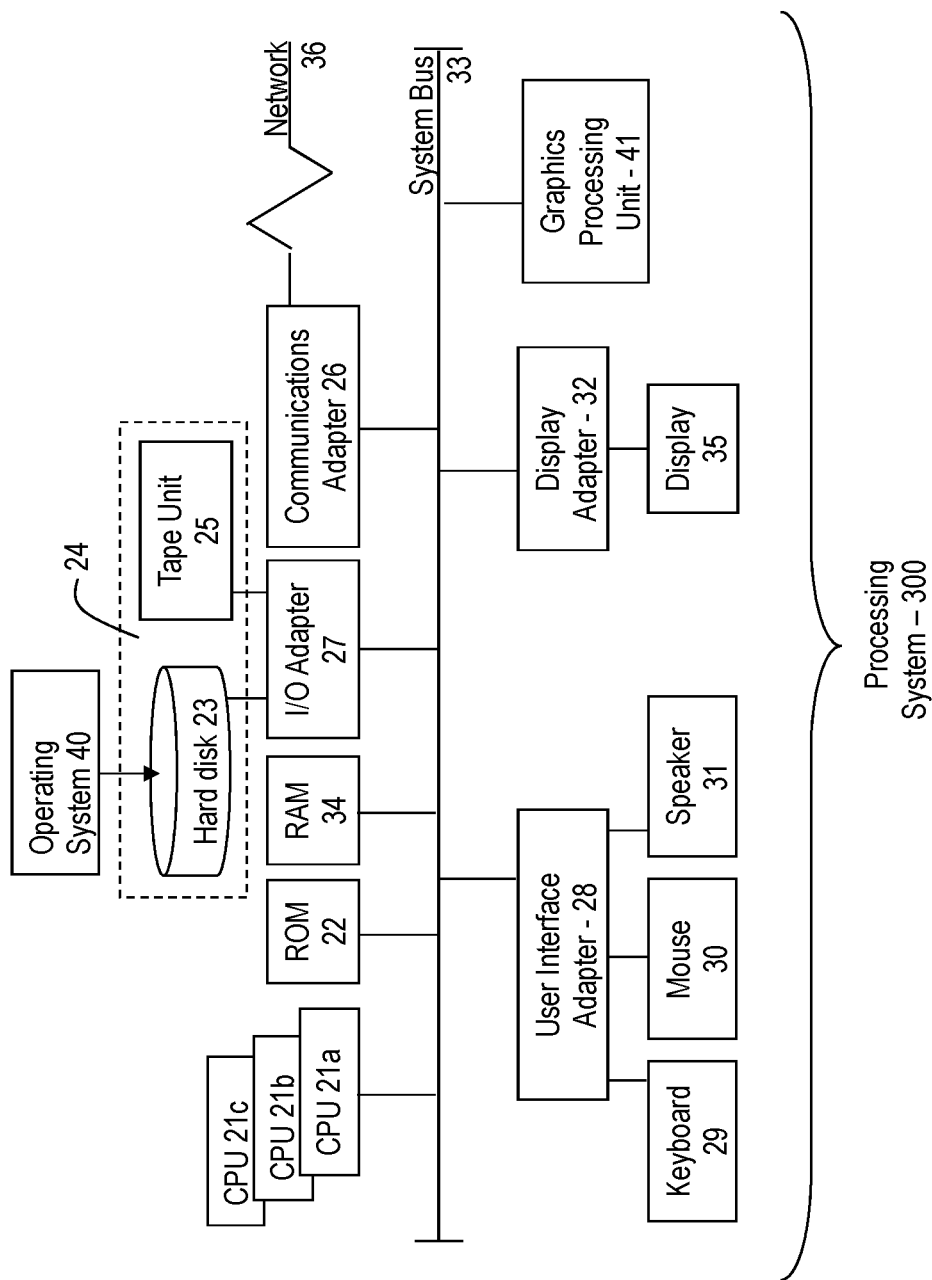
FIG. 3 depicts a block diagram of a computer system for use in implementing one or more embodiments of the present invention.

Referring to FIG. 3, there is shown an embodiment of a processing system 300 for implementing the teachings herein. In this embodiment, the system 300 has one or more central processing units (processors) 21a, 21b, 21c, etc. (collectively or generically referred to as processor(s) 21). In one or more embodiments of the invention, each processor 21 may include a reduced instruction set computer (RISC) microprocessor. Processors 21 are coupled to system memory 34 and various other components via a system bus 33. Read only memory (ROM) 22 is coupled to the system bus 33 and may include a basic input/output system (BIOS), which controls certain basic functions of system 300.

FIG. 3 further depicts an input/output (I/O) adapter 27 and a network adapter 26 coupled to the system bus 33. I/O adapter 27 may be a small computer system interface (SCSI) adapter that communicates with a hard disk 23 and/or tape storage drive 25 or any other similar component. I/O adapter 27, hard disk 23, and tape storage device 25 are collectively referred to herein as mass storage 24. Operating system 40 for execution on the processing system 300 may be stored in mass storage 24. A network adapter 26 interconnects bus 33 with an outside network 36 enabling data processing system 300 to communicate with other such systems. A screen (e.g., a display monitor) 35 is connected to system bus 33 by display adaptor 32, which may include a graphics adapter to improve the performance of graphics intensive applications and a video controller. In one embodiment, adapters 27, 26, and 32 may be connected to one or more I/O busses that are connected to system bus 33 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 33 via user interface adapter 28 and display adapter 32. A keyboard 29, mouse 30, and speaker 31 all interconnected to bus 33 via user interface adapter 28, which may include, for example, a Super I/O chip integrating multiple device adapters into a single integrated circuit.

In exemplary embodiments of the invention, the processing system 300 includes a graphics processing unit 41. Graphics processing unit 41 is a specialized electronic circuit designed to manipulate and alter memory to accelerate the creation of images in a frame buffer intended for output to a display. In general, graphics processing unit 41 is very efficient at manipulating computer graphics and image processing and has a highly parallel structure that makes it more effective than general-purpose CPUs for algorithms where processing of large blocks of data is done in parallel.

Thus, as configured in FIG. 3, the system 300 includes processing capability in the form of processors 21, storage capability including system memory 34 and mass storage 24, input means such as keyboard 29 and mouse 30, and output capability including speaker 31 and display 35. In one embodiment, a portion of system memory 34 and mass storage 24 collectively store an operating system coordinate the functions of the various components shown in FIG. 3.

As mentioned above, resource planning for a facility (e.g., a hospital) is typically performed by analyzing data representative of historical demand in view of facility resources to identify bottlenecks, inefficiencies, and other shortcomings in the process flow or optimization of the use of facility resources to make predictions and suggestions for modifications to resource availability. However, the results of such conventional resource planning analyses are typically presented in the form of reports, charts, spreadsheets and the like. For example, to show patient wait times, the end-user may be shown a simple chart with mean or median points for a period of time. However, many users may find such static forms of data presentation difficult to compile into a comprehensive picture of the operations of the facility. Further, such reports are static and non-interactive, which limits the insights for improving efficiency of a facility that a user may otherwise gain from such analyses. Thus, to facilitate a more interactive and intuitive understanding of facility operations, in exemplary embodiments of the invention, a system for providing an interactive resource plan visualization associated with a facility is provided. In exemplary embodiments of the invention, the system may utilize a cognitive system to analyze facility data to generate a resource plan. The resource plan can be incorporated into a visual representation of the facility that a user can use to view historical, current or predicted resource availability, resource demand, suggestions for modifications to resource availability and optimized procedural plans. For example, in some embodiments of the invention, a three-dimensional representation of the facility may be a virtual reality model of the facility that can allow a user to navigate through and/or view different rooms or portions of the virtual representation of the facility. A virtual reality model/representation of the facility may allow a user to for example, virtually walk down the hallways of the facility and enter different rooms as they would in the real world, or may allow a user to view the facility from the outside and zoom in on various rooms or portions of the facility. According to some embodiments of the inventions, various walls, floors, ceilings may be transparent or semi-transparent or may be capable of being made to be transparent or semi-transparent in response to a user input to, for example, allow a user to see or navigate through walls to view other rooms or portions of the facility. In some embodiments of the invention, an augmented reality system may superimpose virtual content over a real-world view of the facility to allow a user to view aspects of a resource plan, such as predicted demand, available resources, suggested modifications to available resources and visual indications of a procedural plan that the user may follow to execute a predetermined procedure in an efficient manner.

The visual representation of the facility may include representations of available resources (e.g., beds, supplies, employees, etc.) and demand for such resources (e.g., patient queues, indications of occupancy or scheduled occupancy of rooms, supplies earmarked for use or expected use in servicing patents, etc.) so that a user can visually assess the sufficiency of available resources in view of demand or expected demand to, for example, visually identify bottlenecks in efficient servicing of patients. Further, the system can be configured display resources, demands and suggestions in relation to a specified time or timeframe, based on a user input. For example, a user may want to see what the available resources, demands and suggestions for a hospital are expected to look like three months from the current date and in response to a user specifying a future date that is three months in the future, the system may visually display the expected available resources, demands and suggested resource modifications that correspond to the inputted date. In some embodiments of the invention, the user may specify a timeframe and the system may dynamically display the historic or expected future resource availability that corresponds to the time frame. For example, if the user specifies a one-month time frame in the future, the system may present a visual simulation of the expected available resource and demand flows corresponding to the specified future month at a speed that may be adjusted by the user. For example, the changing available resources and demands for a one month period may be dynamically displayed over the course of, for example, five minutes.

According to some embodiments of the invention, the system may also display visual representations of suggestions for resource availability modifications that have been determined by the cognitive system. In other words, if the system determines that the demand for a particular resource significantly exceeds the availability of the resource over a given time period, the system may recommend increasing the availability of the resource to meet the demand. For example, if the system determines that there will be a greatly expected increase in patient hospitalizations two months from now (e.g., based on the prevalence of a new virus), the system may recommend increasing the number of hospital beds that are available for use by the hospital. In some embodiments of the invention, such recommended changes to resource availability can be represented in a different visual style than the generally available resources to provide a visual cue to a user of the recommendation. For example, if a hospital already owns 50 hospital beds and the system recommends that the hospital obtain another 10 beds to accommodate expected future demand, the initial 50 hospital beds may be represented according to a first visual style (e.g., solid images), whereas the recommended 10 beds may be represented according to a second visual style (e.g., semi-transparent). The system can be configured to allow a user to toggle on or off acceptance of a recommended change to resource availability to view the corresponding change to demands. For example, in the previous example, a user may toggle on acceptance of the recommendation to add 10 beds and in response the system may display the effects of other resources and demands (e.g., a decrease in a queue of people waiting for a bed).

Embodiments of the invention can allow a user (e.g., a hospital administrator) to explore a visual representation of a facility, either in reality (i.e., augmented reality) or virtually (e.g., virtual reality), to view historical, present, and/or future expected available resources, demands and/or recommendations based on a time or timeframe specified by the user, as well as ghost images provided as aids in performing tasks efficiently. Such visual representation of the resources, demands, suggestions, and procedural work flows of the facility may allow a user to quickly see the interactions between these aspects at a more granular level and provide the user with insights that the user may not have gleaned from reviewing reports. Reports are generally static and do not allow a user to dynamically and interactively view the flow-on effects or permutations of decisions. However, the interactive visual representation provided by embodiments of the invention can allow a user to explore many different permutations of decisions or recommendations and visualize the expected effects of the decision on other aspects of the facility. For example, in response to the system displaying (e.g., in augmented reality) a suggested addition of one bed to a ward, a user may be able to virtually observe that it may take nurses 15 minutes longer to complete their rounds for that floor (e.g., via a virtual representation of nursing workflows and/or queues within the ward), which can allow the user to make an immediate decision about the potential addition of the bed to the ward based on the impact to the local area. By contrast, reports generally aggregate data at a high level, and so the additional 15 minute impact of the addition of one bed on nurse rounding of a particular ward may be difficult to account for if, for example, a report aggregates and averages rounding times of hundreds or thousands of nurses throughout a facility. Further, the system can provide advantages over the conventional method of resource planning (i.e., generating reports) by dynamically generating and/or adjusting resource plans based on real-time (or intermittent) data obtained from sensors (e.g., facility and vehicle sensors) and third parties (e.g., social media data, weather data, etc.) to update demand projections. Additionally, the interactive system provides further advantages by allowing a user to virtually navigate through a facility to quickly visually recognize problematic areas of the facility, change the time or time frame of the resource plan being visually displayed by the system, and by optionally allowing the user to implement the recommended changes using the system by, for example, providing a user input representing instructions for the system to carry out the recommendation (e.g., order more beds and provide instructions for their delivery and arrangement).

According to some embodiments of the invention, the system may also display a visual indication of one or more steps of a procedural plan. Such visual indications of the virtual performance of steps of a procedural plan may be referred to herein as "ghost images." A procedural plan may be a series of steps to be performed by one or more individuals to carry about some process or procedure. For example, a procedural plan may provide a plan for unloading a plurality of boxes from a truck, where different boxes are to be taken to different rooms within a facility. The procedural plan may map out the order that the boxes are to be removed from the truck and the route through the facility each box is to be taken to reach their respective destinations. The system may present ghost images (e.g., via an augmented reality device) for a user to follow that correspond to the procedural plan. For example, a ghost image of a virtual person unloading a first virtual box from the truck may be presented in an augmented reality device, such that the wearer of the augmented reality device can follow in the footsteps of the ghost image by picking up the corresponding real box and then following the path taken by the ghost image to the delivery destination of the box. In this way, the system can allow users to perform predetermined tasks and procedures more efficiently by providing an optimized visual guide of the task or procedure for the user to follow.

Figure 4:
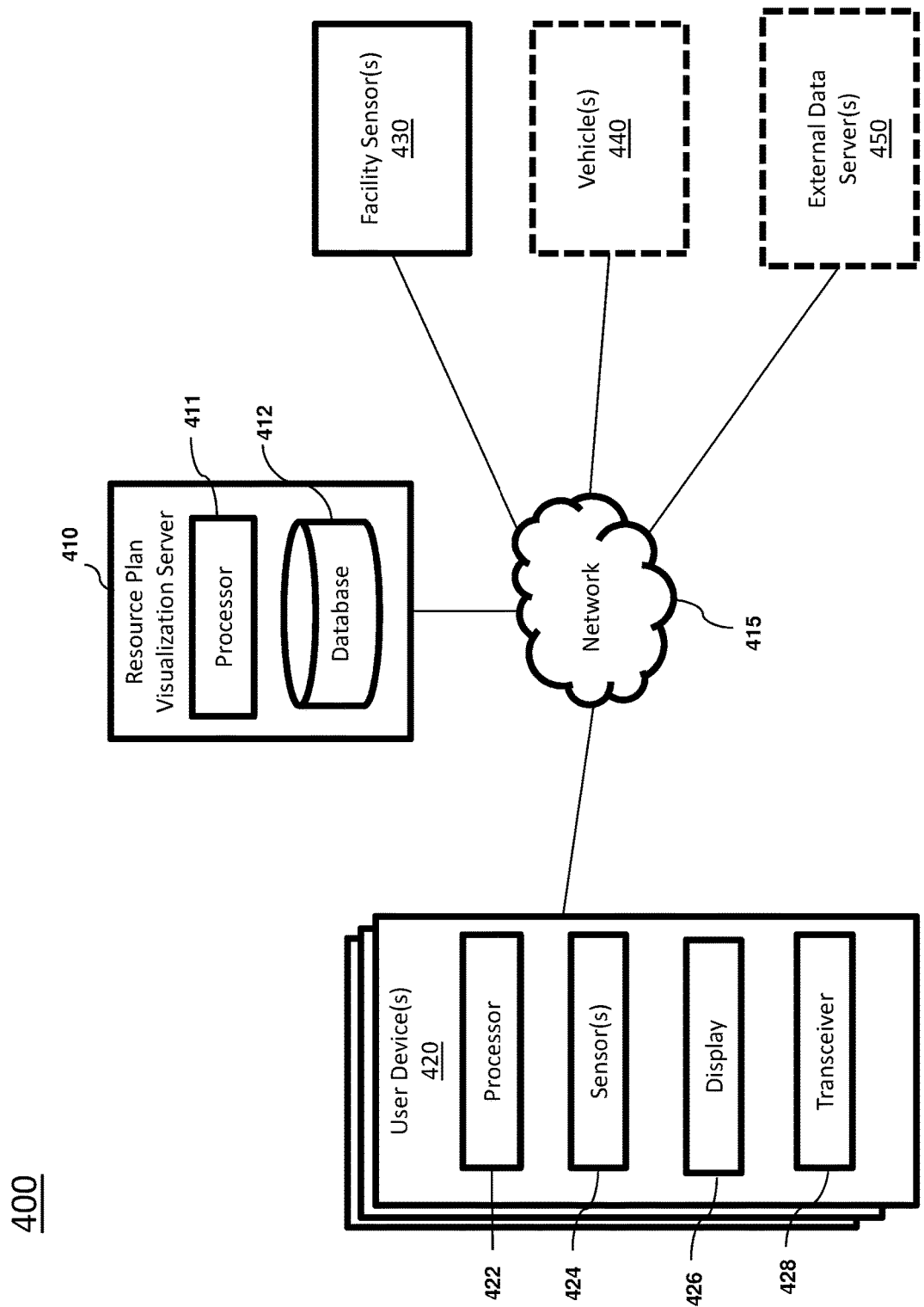
FIG. 4 depicts a system upon which providing an interactive resource plan visualization associated with a facility may be implemented according to one or more embodiments of the present invention.

Turning now to FIG. 4, a system 400 for providing an interactive resource plan visualization associated with a facility will now be described in accordance with an embodiment. The system 400 includes a resource plan visualization server 410 in communication with user devices 420, a facility sensor(s) 430, and vehicle(s) 440 and external data server(s) 450 via communications network 415. According to some embodiments of the invention, system 400 may not include vehicle(s) 440 and/or external data server(s) 450. The communications network 415 may be one or more of, or a combination of, public (e.g., Internet), private (e.g., local area network, wide area network, virtual private network), and may include wireless and wireline transmission systems (e.g., satellite, cellular network, terrestrial networks, etc.). As will be described in greater detail herein, the resource plan visualization server 410 may generate a visualization of a facility (e.g., generating a virtual reality model of the facility or superimposing virtual content over a real world view of the facility in augmented reality) and an associated resource plan that provides visual indications of available resources, demand for resources and/or suggestions for optimizing or improving the use of resources in view of the demand. The resource plan visualization server 410 may also generate a procedural plan with associated ghost images that can be displayed by an augmented reality device to provide a guide to a user to efficiently perform a task or process associated with the procedural plan. According to some embodiments of the invention, user devices 420 are configured to display the visual representation of the facility (which may be referred to as a "virtual facility") generated by the resource plan visualization server 410 and allow a user to interact with the virtual facility by for example, navigating through the virtual facility or viewing a portion (e.g., a selected room, building or wing) of the virtual facility. In some embodiments of the invention, a user device 420 can be an augmented reality device that is configured to superimpose virtual content (e.g., representations of demand, available resources, suggestions and/or ghost images associated with a procedural plan) over a view of the facility.

In exemplary embodiments of the invention, user devices 420 can include, but are not limited to, a smartphone, a wearable device such as a smartwatch, a virtual reality headset, an augmented reality headset, a tablet, a computer system such as the one shown in FIG. 3, a television, or any other suitable electronic device that may be used to display virtual content in virtual or augmented reality. The user device 420 includes a processor 422, one or more sensors 424, a display 426 and a transceiver 428. The sensors 424 can include one or more of an image capture device (e.g., digital camera) for obtaining images and/or videos, a microphone for obtaining audio recordings, and a location sensor for obtaining location data of the user device (e.g., GPS coordinates). User devices 420 can include an input device, such as a keyboard (either physical or digital) for receiving user input text. Text can also be input orally via a microphone using voice recognition. In some embodiments of the invention, display 426 is configured to display images and/or video. In some embodiments of the invention, display 426 can be a touchscreen that may be configured to detect tactile user inputs (e.g., typing, pressing, swiping, etc.). Transceiver 428 can be configured to allow a user device 420 to communicate with other devices via communications network 415 (e.g., via Wi-Fi, cellular communications, etc.). As will be understood by those of skill in the art, an augmented reality device can be a wearable device that includes an image capture device for obtaining images of the physical world, and a see-through display that is capable of displaying virtual content that is superimposed over the view of the physical world. A virtual reality device can be a wearable device that includes a display that is configured to display a virtual environment, such as a virtual facility, and can include user input controls for navigating about the virtual environment or changing aspects of the view of the virtual environment (e.g., zooming in, making walls transparent, etc.).

In some embodiments of the invention, a resource plan visualization server 410 can include at least one processor 411 and a memory 412 for executing the functions of the resource plan visualization server 410 described herein. According to some embodiments of the invention, the resource plan visualization server 410 can store a representation of a facility, such as a model of the facility that can be displayed as a virtual model in virtual reality, or can be used by an augmented reality device to superimpose virtual content over a view of the physical world (e.g., based on the location and/or orientation of the augmented reality device). The representation may be preprogrammed by a user or may be created by, for example, obtaining measurements and visuals from sensors (e.g., laser measurement devices, etc.) and image capture devices (e.g., cameras) and combining them into a virtual model of the facility. According to some embodiments, a virtual representation of a facility may be auto-generated from building schematics and architectural blueprints. For example, as will be appreciated by those of skill in the art, tools that convert static two dimensional (2D) images into three dimensional (3D) virtual worlds may be used to generate a 3D representation that can be used for generating a virtual reality facility or used for creating content in an augmented reality system. In some embodiments, a representation of a facility that is created via automated methods may be modified by a developer using software to for example, add interior décor, colorize portions of the representation, make adjustments to the layout of the representation or any other such modifications.

According to some embodiments of the invention, the resource plan visualization server 410 can be configured to generate a resource plan and/or procedural plan by performing a cognitive analysis based on the available resources, known demands (e.g., previously scheduled procedures, appointments or other events), and/or historical facility data. For example, in some embodiments, the resource plan visualization server 410 can be implemented as a programmable computer (e.g., processing system 300 shown in FIG. 3) having a cognitive system (e.g., cognitive system 600) that includes algorithms configured and arranged to carry out certain dynamic and cognitive methodologies in accordance with aspects of the invention. More specifically, the cognitive system can include algorithms (e.g., machine learning algorithms) configured to make cognitive determinations about the presence people (e.g., patients) or items (e.g., medical equipment) in a room or location, an activity being performed (e.g., waiting, using equipment, serving a patient, preparing a room for use, etc.), and/or inferences about probable future events (e.g., determining that a patient will need to see various specialists, requiring the use of various equipment, supplies and medicine, for example based on information about the patient's condition). The cognitive system may base such determinations on stored records and sensed data (e.g., data from facility sensors 430, vehicles 440 and/or external data servers 450). According to some embodiments, such cognitive analysis can be used to predict future demand of resources and to generate resource/procedural plans. As will be understood by those of skill in the art, machine learning algorithms utilized by the cognitive system may be developed using supervised or unsupervised training. According to some embodiments, supervised machine learning may be used predict demand and to identify and/or classify objects and people (e.g., for use in demand prediction). For example, supervised machine learning may be used to teach the system to distinguish between patients and staff at a hospital based on the presence of badges, logos, clothing and/or equipment associated with an individual in an image. Once trained, the machine learning model may allow the system to receive images (e.g., from security cameras within a facility) and then may automatically identify which individuals in the images are patients and which individual are staff. This information may then be utilized by the cognitive system in generating a resource plan and/or procedural plan, by for example, incorporating the information into calculations relating to resources (e.g., available staff) and demand (e.g., incoming patients). In some embodiments, resource plan visualization server 410 may generate a resource plan using operations research techniques and/or optimization techniques, similar to approaches shown in, for example, U.S. Patent Pub. No. 2016/035049.

The phrase "machine learning" broadly describes a function of an electronic system that learns from data. A machine learning system, engine, or module can include a trainable machine learning algorithm that can be trained, such as in an external cloud environment, to learn currently unknown functional relationships between inputs and outputs.

Machine learning functionality can be implemented using an artificial neural network (ANN) that has the capability to be trained to perform a currently unknown function. In machine learning and cognitive science, ANNs are a family of statistical learning models inspired by the biological neural networks of animals, and in particular the brain. ANNs can be used to estimate or approximate systems and functions that depend on a large number of inputs.

ANNs can be embodied as so-called "neuromorphic" systems of interconnected processor elements that act as simulated "neurons" and exchange "messages" between each other in the form of electronic signals. Similar to the so-called "plasticity" of synaptic neurotransmitter connections that carry messages between biological neurons, the connections in ANNs that carry electronic messages between simulated neurons are provided with numeric weights that correspond to the strength or weakness of a given connection. The weights can be adjusted and tuned based at least in part on experience, making ANNs adaptive to inputs and capable of learning. For example, an ANN for handwriting recognition is defined by a set of input neurons that can be activated by the pixels of an input image. After being weighted and transformed by a function determined by the network's designer, the activation of these input neurons is then passed to other downstream neurons, which are often referred to as "hidden" neurons. This process is repeated until an output neuron is activated. The activated output neuron determines which character was read.

In certain embodiments of the invention, some or all of the processes performed by resource plan visualization server 410 are performed by one or more specialized computers (e.g., one or more specialized processing units, a specialized computer with text data component, etc.) for carrying out defined tasks related to machine learning. In some embodiments of the invention, system 400 and/or components of the system are employed to solve new problems that arise through advancements in technologies mentioned above.

Generation of the resource plan can include predicting future demand, generating recommendations for modifications to available resources (e.g., a recommendation to buy more beds, schedule more staff to work, etc.), and generating instructions for providing a visualization of the resource plan and/or procedural plan. As will be understood by those of skill in the art, various statistical methods can be applied by the resource plan visualization server 410 to determine predicted demand, recommendations for modifications to available resources, and/or optimized steps for performing a task or procedure based on one or more of the demand, available resources, and constraints associated with a procedure (e.g., a surgery). For example, in some embodiments, a cumulative distribution can be used to determine how many hospital beds of a hospital are filled up over a predetermined period. In some embodiments, the system may use optimization and operations research techniques such as mixed integer programming (MIP) to generate a resource plan. According to some embodiments of the invention, the resource plan visualization server 410 can dynamically generate and/or update a resource plan or procedural plan in real-time or intermittently based on sensor data received from facility sensor(s) 430, vehicle(s) 440 and external data server(s) 450. For example, if facility sensors 430 detect a large influx of patients into an emergency room of the facility or a number of ambulances (i.e., vehicles 440) provide data indicating an influx of new patients, the resource plan visualization server 410 may immediately update the resource plan to show greater demand on other services of the facility (e.g., hospital beds, medical supplies, pharmacy, etc.) over the next hours, days or weeks.

According to some embodiments, a resource plan may include a procedural plan for performing a series of steps to achieve a predetermined goal. For example, a procedural plan may be a plan for performing a scheduled surgery or a plan for unloading a supply truck. A procedural plan can include the resources needed to perform the procedure, including for example, one or more of staff members, supplies, rooms, and/or equipment. A procedural plan can also include a list of steps to be followed by a user of the system, such as for example, taking a patient to various locations in a facility to carry out various tasks (e.g., taking vitals, obtaining x-rays, drawing blood, etc.) or various sequential steps used in performing a surgical procedure. A procedural plan can be generated by resource plan visualization server 410 based on known scheduled procedures, known steps associated with a given procedure, and the scheduled or available resources needed to perform the procedural plan. According to some embodiments, resource plan visualization server 410 can modify a procedural plan based on real-time observations made by facility sensors 430 or previous observations made in relation to similar past procedures. For example, if for a given surgical procedure, the resource plan visualization server 410 determines that better outcomes have been observed if a patient's vitals are measured before blood is drawn, then resource plan visualization server may modify procedural plans for future procedures to reorder the steps of the plan accordingly. Similarly, if in the middle of a surgery, a facility sensor 430 detects an abnormal response from a patient, the resource plan visualization server 410 may modify the procedural plan to perform extra steps to address the abnormal response. In this way, resource plan visualization server 410 can be configured to optimize procedural plans in attempt to make them the most efficient and effective in terms of the amount of resources and/or time needed to achieve the desired outcome. Based on an optimized procedural plan, the resource visualization server 410 can be configured to generate a visualization of a virtual execution of the procedural plan that can be visually represented as one or more semi-transparent images (which may be referred to as "ghost images") displayed by, for example, an augmented reality device. For example, if a procedural plan dictates that a surgical patient should have their vitals taken in a first hospital room, be taken for x-rays in a second hospital room and then have blood drawn in a third hospital room, the resource plan visualization server 410 may cause a user device 420 to display ghost images of the patient or nurse sequentially walking through the hospital from the first room to the second room to the third room to visually show the steps to be taken. The system may track the user's movements and activities (e.g., via facility sensors 430), and may visually present the next sequential step of a procedural plan after the user has completed the current step. The procedural plan can be thought of as a map to be followed by a user in order to attempt to achieve the most efficient execution of the procedure, as determined by the resource plan visualization server 410. As such, user device 420 can display ghost images representative of the steps or actions determined by the system (e.g., resource plan visualization server 410) for a user to follow. Such procedural plans and ghost images can include steps for, for example, sequentially guiding a patient or customer to one or more rooms or points of a facility or performing a sequential series of steps (e.g., a series of steps to perform a surgery or a series of steps to unload boxes from a truck to be delivered to one or more locations within the facility). Because the ghost images represent the determined optimal path to perform the given procedure, a user of user device 420 (e.g., an augmented reality device) can follow the ghost images presented by the user device 420 to perform the procedure in an efficient manner.

According to some embodiments of the invention, resource plan visualization server 410 can generate a visual representation of aspects of a resource plan within a facility (e.g., via virtual or augmented reality) that incorporates one or more indications of available resources, demands and/or suggestions to modify available resources of the resource plan into the visualization. For example, available resources can be represented as the virtual presence (i.e., virtual content in virtual reality or augmented reality) of one or more employees, supplies, pieces of equipment or furniture and demand can be represented as the virtual presence of one or more customers, patients or objects (e.g., samples waiting to be processed by a machine or technician). Such virtual content can be viewed by a user locally (e.g., a user positioned within a ward can view the virtual resources etc. within that ward), such that resources, supplies, people and the like may virtually appear approximately as they would in real life. Alternatively, virtual content may be viewed from a zoomed out perspective, such that for example, a user may virtually view the entire facility or a portion of the facility and resources, supplies, people and the like may be displayed as icons, colored dots, or the like, to allow a user to, for example, perform a comparison of the state of various portions of a facility (e.g., rooms) each one another. According to some embodiments, a user may toggle between a local view (e.g., an augmented reality view of a room the user is in) and a zoomed out view (e.g., a virtual reality view of a representation of the entire facility). In some embodiments, rooms or portions of a facility may be associated with different colors, icons or images that denote different information. For example, in a zoomed out view of a hospital, each ward may be displayed as a box having a circular dot for every nurse in the ward and a rectangle for every bed. In some embodiments, colors can be used to convey additional information. For example, a red dot or a red rectangle may represent a deficiency of nurses or beds, respectively. Similarly, the boxes associated with wards may have different colors based on whether the ward meets a desired threshold (e.g., a ratio of nurses to beds, a maximum rounding time, etc.), allowing a user to quickly make a visual assessment and comparison of wards to one another. The desired thresholds and/or shapes and colors associated with virtual content may be configurable by a user. Further, in some embodiments, resources, demands, queueing times, and any other such objects or metrics may be represented as numbers (e.g., "available nursing staff=10"), graphs (e.g., bar graphs), images or some combination of the above. In some embodiments, suggestions to modify available resources may be represented as images, such as an image of an extra employee, machine, supplies, bed, or the like presented in virtual reality or augmented reality. According to some embodiments of the invention, suggestions to modify available resources may be represented according to a different visual style than the representation of current or predicted available resources. For example, available resources may be virtually represented as solid objects whereas suggested resources may be represented as transparent or semi-transparent objects. A transparent or semi-transparent representation of an object, person, or item may be referred to as a "ghost image."

According to some embodiments resource plan visualization server 410 may be configured to communicate with one or more external data servers 450 that can optionally receive and process orders of additional resources. Accordingly, in some embodiments of the invention, resource plan visualization server 410 can be configured to automatically place an order for new resources in response to a user selecting and accepting a recommendation presented in the visual representation of the facility (e.g., via user device 420). Likewise, if the recommendation is to schedule an extra employee, the resource plan visualization server 410 can be configured to access and adjust employee schedules to schedule a recommended employee upon acceptance of the suggestion by the user. According to some embodiments, resource plan visualization server 410 may allow a user to modify the suggestion prior to accepting it, by for example, changing the number of recommended resources, the type of recommended resources, or the location of recommended resources. In response to receiving a user input to change a recommended resource, the resource plan visualization server 410 may be configured to adjust the resource plan and display the effects (e.g., predicted demand, etc.) of the suggested change in the visual representation of the facility. In this way, a user of the system can visually observe the effects of their suggested resource changes on a portion of or on the entire facility prior to accepting the recommendation. According to some embodiments, accepting a recommendation may cause the resource plan visualization server 410 to automatically communicate instructions to one or more people. For example, a notification may be sent to an employee who has been scheduled on a shift or instructions explaining where to deliver or place an ordered item may be delivered to a merchant selling the item.

In some embodiments of the invention, a user device 420 can be a virtual reality headset. As will be appreciated by those of skill in the art, a virtual reality headset can display a virtual world that has a changing view based on what direction the user's head is oriented. The user device 420 may include user input devices (e.g., buttons, oral commands, etc.) that allow a user to navigate through the virtual facility or may allow a user to rotate, zoom, make selected walls transparent, or otherwise manipulate a view of the virtual facility. Thus, in such embodiments of the invention, the system will allow a remote user to explore the virtual facility to observe a past, current or future resource plan. A resource plan can be understood to be one or more of a representation of the available resources of the facility, the demand, and/or suggestions for changes to the available resources, in relation to a specified time or time frame.

In some embodiments of the invention, a user device 420 can be an augmented reality (AR) headset. As will be appreciated by those of skill in the art, an augmented reality headset can include a see-through display that superimposes images over a view of the real world. In such embodiments of the invention, the system (e.g., resource plan visualization server 410) may store a floorplan, blueprints, or other plans of the facility and may generate visualizations based on the user's location within the facility. For example, if the user is standing at a pharmacy within a hospital, the user device 420 may display a representation of virtual resources (e.g., a virtual representation of a pharmacist and a pharmacy technician) and a representation of virtual demand (e.g., a queue of expected customers) to provide the user with a sense of how busy the pharmacy is expected to be at a specified time. Thus, in such embodiments of the invention, the system can allow a user that is physically on-site at the facility to view location-based aspects of a resource plan as the user moves about the facility. For any given location, the user can input a selection of a time or timeframe to view the details of the resource plan at that location that corresponds to the selected time or timeframe. Thus, if the user wants to know how busy the pharmacy is predicted to be in a month, the user may for example, turn a dial or press a button on the user device 420 until the selected time corresponds to one month from now, at which point the user device 420 can display the scheduled resources (e.g., which employees are scheduled to work that day), the predicted demand (e.g., the length of a queue based on the predicted rate of service) and any suggested resource modifications (e.g., a suggestion to schedule an extra pharmacy technician to work that day). Furthermore, in some embodiments of the invention, an AR headset can be configured to display aspects of a resource plan, such as ghost images of a procedural plan that represent an optimal path for carrying out a given process or procedure, as determined by the resource plan visualization server 410. Thus, according to embodiments of the invention, an AR headset worn by a user can display ghost images that the user can copy or follow within the facility to carry out the procedure. For example, the system may aid a nurse in guiding a patient from room to room within a hospital based on a sequence of tests the patient needs, aid a doctor in performing a surgery by displaying ghost images of the steps of surgery to be followed by the doctor, aid an individual in unloading a truck of boxes by providing ghost images that show the individual a path to a destination for each respective box that is unloaded, or any other such type of procedure or activity that may be carried out in a facility.

According to some embodiments of the invention, facility sensors 430 can include sensors disposed about equipment associated with the facility, such as medical equipment that is capable of obtaining readings (e.g., biometric signals from patients). In some embodiments of the invention, facility sensors 430 can include one or more sensors disposed about a facility that can detect for example, the presence of a number of people at a location (e.g., number of people in a waiting room), the identification of a person (e.g., via facial recognition), or the presence of a number of objects or items at a location (e.g., number of samples waiting to be processed). Facility sensors 430 can include one or more of a camera, microphone, a bar code scanner, an RFID scanner, an infrared camera, a forward-looking infrared (FLIR) camera for heat detection, a time-of-flight camera for measuring distance, a radar sensor, a LiDAR sensor, a temperature sensor, a humidity sensor, a motion sensor or the like. In some embodiments of the invention, all individuals in a facility may be required to carry a RFID tag and the system may track everyone's position in the facility over time. Facility sensors 430 may also include devices that can receive user inputs, such as computers, laptops, touchscreens, and devices utilizing voice-recognition software. Accordingly, in some embodiments, facility sensors 430 may generate data streams from staff, customers, patients as well as non-human assets (e.g., machines, devices, etc.). According to some embodiments of the invention, the resource plan visualization server 410 can use sensor data to determine one or more current levels of demand of available supply associated with the facility at a given time. In some embodiments, identification of individuals and/or objects can be cross-referenced with stored system data to predict aspects of demand. For example, if the system detects that John Doe has entered a hospital, the resource plan visualization server 410 may predict the resources John Doe will need based on the previous visits made by John Doe or based on other information (e.g., medical history) associated with John Doe. Facility sensors 430 may also be used to observe the execution of a procedural plan to identify bottlenecks or inefficiencies in the plan that may be improved upon by resource plan visualization server 410. For example, if various people undergo the same medical procedure, the facility sensors 430 may observe that there is a lot of wasted time during the medical procedure because several patients are waiting to see a cardiologist before moving on to other parts of the medical procedure. Thus, the resource plan visualization server 410 may adjust procedural plans for future patients of the medical procedure to adequately space them apart in time so that each patient may see a cardiologist without having to wait a significant amount of time. In this way, the facility sensors 430 can be used to detect information that can be used by resource plan visualization server 410 to identify bottlenecks in processes or shortages in available resources and make changes to resource plans and/or procedural plans accordingly.

Similar to the facility sensors 430, vehicles 440 (e.g., ambulances, delivery trucks, etc.), may include sensors and may intermittently provide data to resource plan visualization server 410 that can be used to forecast demand, such as the identification of an incoming patient, the patient's condition, and the location and/or expected time of arrival of the vehicle. Likewise, other types of vehicles 440, such as delivery trucks, may communication information about cargo that can be used to predict demand and/or available resources, such as a number of samples to be processed by a facility or a number of boxes of parts, materials or other objects to be used to provide a resupply.

According to some embodiments, external data server(s) 450 may also provide information that can be used by resource plan visualization server 410 in determining or adjusting a resource plan. For example, a weather service server may provide real-time weather updates that may be used to predict in increase or decrease in the number of expected patients to a hospital. Traffic updates provided by a traffic monitoring service may also be used to predict changes to demand. Social media servers may also provide data that can be used in predicting demand, for example, if many people in a particular locality begin reporting or discussing a common health problem on social media, the resource plan visualization server 410 may determine an underlying cause (e.g., a contaminated food source) and predict an influx of an increased number of patients have similar conditions.

Figure 5:
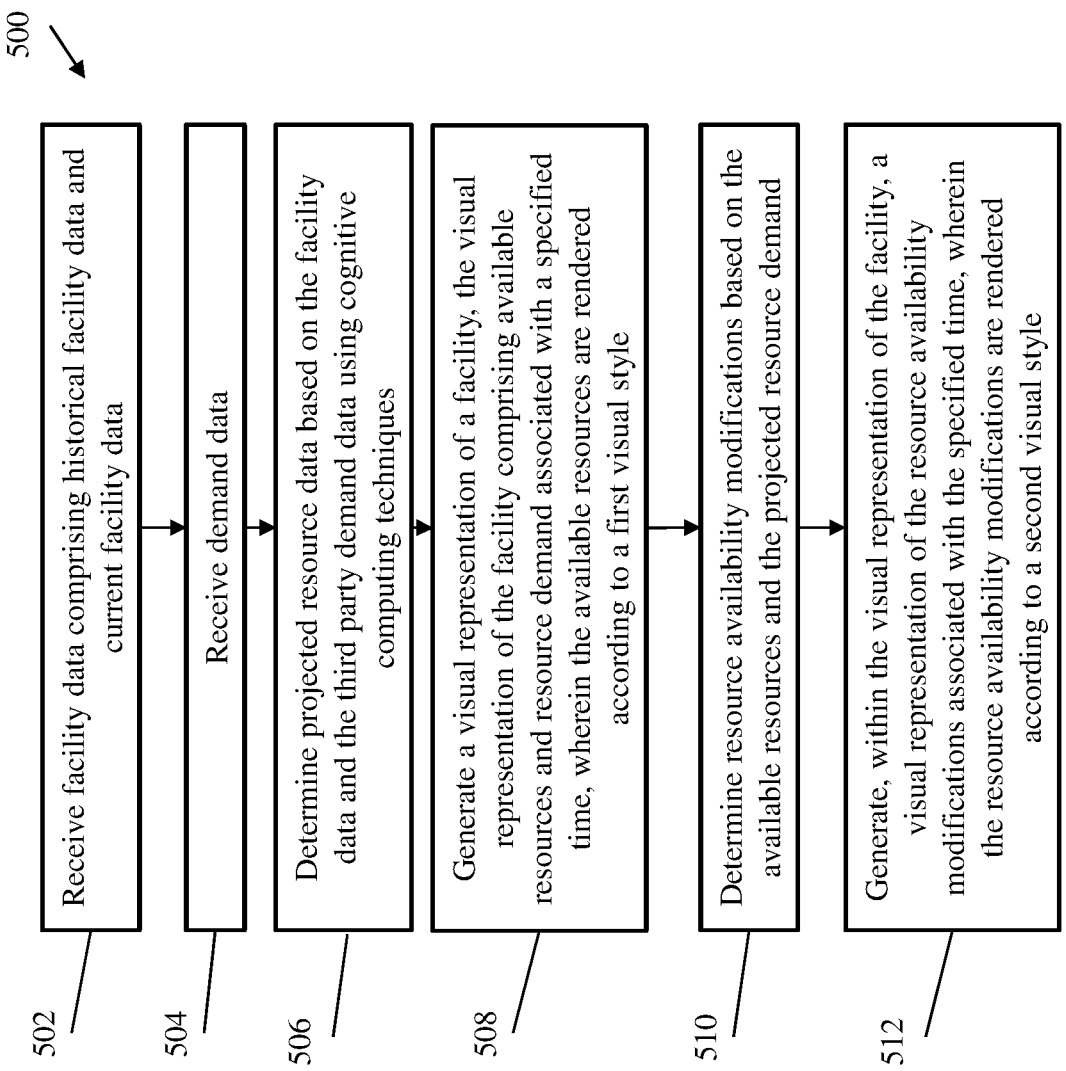
FIG. 5 depicts a flow diagram of a method for providing an interactive resource plan visualization associated with a facility according to one or more embodiments of the invention.

Turning now to FIG. 5, a flow diagram of a method 500 for providing an interactive resource plan visualization associated with a facility in accordance with an embodiment is shown. In one or more embodiments of the present invention, the method 500 may be embodied in software that is executed by computer elements located within a network that may reside in the cloud, such as the cloud computing environment 50 described herein above and illustrated in FIGS. 1 and 2. In other embodiments of the invention, the computer elements may reside on a computer system or processing system, such as the processing system 300 described herein above and illustrated in FIG. 3, or in some other type of computing or processing environment.

The method 500 begins at block 502 and includes receiving (e.g., by a processor of resource plan visualization server 410) facility data that includes historical facility data and current facility data. According to some embodiments of the invention, the current facility data can include data representative of the currently available resources and current resource demand. For example, data representative of the currently available resources may include information about how many hospital beds, examination rooms, emergency rooms, operating rooms and the like are available for use, as well as any planned future use of such resources. Data representative of the currently available resources may also include data about which employees are working at what times and the tasks and schedules of those employees (e.g., a surgeon surgeries scheduled today at 10:00 am and 3:00 pm). Current resource demand can include, for example, information that is known about how many patients are waiting to be seen, what their conditions are, and what resources are expected to be needed in treating the patient. For example, if a particular with a known condition has signed in to be seen by a doctor, the system may determine that there is a current demand for the doctor, one or more associated nurses, various spaces or rooms that the patient is expected to occupy (e.g., a waiting room, an X-ray room, a lab for having blood drawn, and a hospital bed) based on the condition of the patient, and any equipment, supplies or medicine that is expected to be utilized in attending to the patient. According to some embodiments, current facility data can be received via user inputs (e.g., a patient filling out a form upon checking in to a hospital, vital signs of a patient taken by a nurse or the like) and/or derived from data obtained by facility sensor(s) 430 (e.g., detection of how many rooms or beds are occupied, which employees are occupied, a quantity of medicine or supplies in inventory, and the like). Historical facility data may be data that is similar to the current facility data but that has been collected in the past and stored by the system.

At block 504, the method includes receiving (e.g., by resource plan visualization server 410) demand data. The received demand data may be data that may be indicative of future resource demands. In some embodiments, demand data may include or be derived from data obtained from one or more facility sensors 430, such as for example, a detected number of people entering a facility, a detected number of people traveling on an elevator to a selected floor, detected audio signals indicative of future events (e.g., a doctor stating "This patient needs to be X-rayed"), or any other such indications of demands for services or resources that may be inferred based on data obtained by facility sensors 430. For example, in some embodiments, an infrared sensor or electronic thermometer may determine that a patient has a fever, and based on this information may predict an increase demand for a medication to address the fever. As will be understood by those of skill in the art, various algorithms and/or models may be used to predict future demand based on observations from facility sensors 430. According to some embodiments, as described previously above, resource plan visualization server 410 may use supervised machine learning models to determine predictions of future demand. In some embodiments, demand data may include or be derived from data received from one or more vehicle(s) 440. For example, ambulances may transmit information about one or more patients in transit, the condition of the patient(s), the location of the vehicle, the destination of the vehicle and the estimated time of arrival of the vehicle. For example, the system may receive data from a vehicle 440 that indicates that the patient is having an asthma attack and the vehicle will arrive at the hospital in 15 minutes, and from this received data the system may determine that there will be additional demand in 15 minutes for various resources (e.g., staff, nurses, doctors, rooms, medical equipment, prescription medicine, etc.) associated with treating this patient for this condition. According to some embodiments of the invention, the demand data can include or be derived from data obtained from one or more external data servers 450, such as at least one of social media data, weather data, traffic data, seasonal statistics provided by a local health authority (e.g., historically higher probabilities of encountering patients having flu during certain months), travel statistics from local airports (e.g., a sudden influx of people from tropical climates), emergency services data (e.g., police statistics for estimating increases and decreases in violent trauma incidents) and deployed ambulance data. For example, the system may determine that demand for resources will increase based on incoming dangerous weather or prevalent conversation on social media about the spread of some condition (e.g., the flu). Deployed ambulance data can include a GPS location and a patient diagnosis of one or more deployed ambulances.

At block 506, the method includes determining (e.g., by resource plan visualization server 410) projected resource demand based on the facility data and the external demand data and using cognitive computing techniques. For example, resource plan visualization server 410 may run one or more statistical models to predict future demand based on historical and current data. In some embodiments, resource plan visualization server 410 may determine projected resource demand using a combination of statistical models and supervised machine learning. According to some embodiments, the projected resource demand can include the predicted demand for the available resources in relation to one or more a future time periods, such as for example, in an hour from the current time, the next day, the next week, or at some future time or date specified by a user. In some embodiments, projected resource demand can also be determined based on planned events such as scheduled events (e.g., planned surgeries) or macro events (e.g., a local government is planning to reduce medical infrastructure spending by 20% in the next fiscal year, an area near the facility has been rezoned from industrial to residential, the local area is receiving a large population of migrants, or other such large scale events).

At block 508, the method includes generating (e.g., by resource plan visualization server 410) a visual representation of a facility. According to some embodiments of the invention, the visual representation of the facility can include available resources and resource demand associated with a specified time. For example, available resources can be presented as an image in virtual reality or highlighted/annotated in augmented reality. Likewise, in some embodiments of the invention, resource demand can be depicted as, for example, a queue of patients or customers, a resource that is worn out (e.g., an x-ray machine that is showing significant wear and tear from lack of maintenance and/or overuse), expressions on virtual representations of staff (e.g., a nurse is depicted having a sad face to represent being overburdened from long working hours), an amount of resources required for a task (e.g., time needed for a patient in an intensive care unit bed, time required using a machine, an amount of medication needed, etc.) or any other form of representation that conveys a need or a demand. In some embodiments of the invention, the available resources can be rendered according to a first visual style. In some embodiments of the invention, the available resources can include for example, at least one of hospital beds, operation rooms, surgical equipment, doctors, nurses, medication and medical supplies. According to some embodiments of the invention, the first visual style can be an opaque image, and the second visual style can be a semi-transparent image that defines the contours of the image but is substantially see-through (i.e., a "ghost image"). It will be understood that these visual styles are exemplary and may other types of visual styles may be used by the system.

According to some embodiments of the invention, the visual representation of the facility can be a three-dimensional representation of the facility configured to be displayed by a computing device (e.g., user device 420). In some embodiments of the invention, a view of the three-dimensional representation is configured to be modified by a user of the computing device to view different portions of the three-dimensional representation of the facility. For example, the computing device could be one of a desktop computer, a laptop, a tablet, a mobile device, a wearable device, a smart watch, a virtual reality device or an augmented reality device. In the case of an augmented reality device, the physical facility may be viewable through a see-through display of the augmented reality device and the visual representation of the facility may include superimposing virtual content on top of the real-world display of the facility.

At block 510, the method includes determining (e.g., by resource plan visualization server 410) resource availability modifications based on the available resources and the projected resource demand. For example, if the resource plan visualization server 410 determines there will not be enough hospital beds to accommodate the expected future demand at a particular future time, the system may display a recommendation to add more hospital beds. As will be understood, the nature of the resource availability modifications may vary greatly based on the data and type of facility at issue.

At block 512, the method includes generating (e.g., by resource plan visualization server 410) a visual representation of the resource availability modifications associated with the specified time within the visual representation of the facility. According to some embodiments, the resource availability modifications can be rendered according to a second visual style. For example, in some embodiments of the invention, resource availability modifications may be displayed as ghost objects.

According to some embodiments of the invention, the method 500 can further include receiving a user input (e.g., via user device 420) indicative of a different specified time and modifying at least one of the visual representation of the available resources, resource demand and resource availability modifications to represent data associated with the different specified time. For example, a user may select a view of the expected resources and demand tomorrow, next week, next month, or at any other time.

Figure 6:
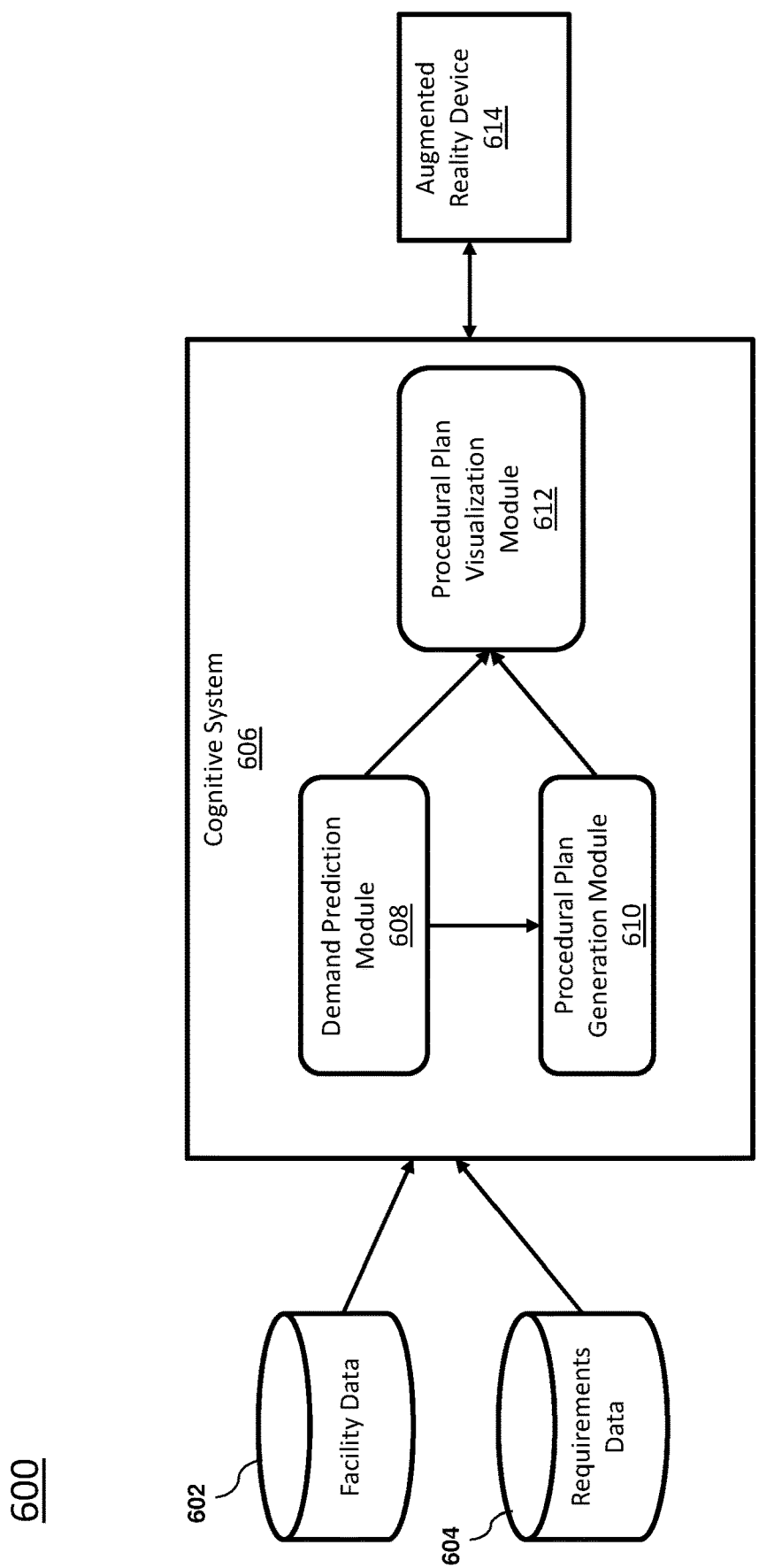
FIG. 6 depicts a system upon which providing procedural plan visualization associated with a facility may be implemented according to one or more embodiments of the present invention.

FIG. 6 depicts system 600 upon which providing a procedural plan visualization associated with a facility may be implemented according to one or more embodiments of the invention. In one or more embodiments of the present invention, the functions performed by system 600 may be embodied in software that is executed by computer elements located within a network that may reside in the cloud, such as the cloud computing environment 50 described herein above and illustrated in FIGS. 1 and 2. In other embodiments of the invention, the computer elements may reside on a computer system or processing system, such as the processing system 300 described herein above and illustrated in FIG. 3, or in some other type of computing or processing environment.

In some embodiments of the invention, a cognitive system 606 may generate a procedural plan and an associated visualization of the procedural plan based on facility data and requirements data received from facility data storage 602 and requirements data storage 604. According to some embodiments, a cognitive system 606 may be included in a resource plan visualization server 410. According to some embodiments, facility data storage 602 and/or requirements data storage 604 may be embodied in memory of resource plan visualization server 410. Facility data can include historical and current data such as for example, historical facility data (e.g., historical records regarding resources, supplies, demand, etc.), historical data of other facilities, historical and current data from facility sensors 430, vehicles 440 and external data servers 450, and other such data. For example, in the context of a medical facility, data received or accessed by the cognitive system 606 can include historical surgery data, physiological historical data for patients, electronic medical records, social media data of patients or other local users, surgeon or other medical staff data, and sensor data. The cognitive system 606 may also receive (e.g., from sensor data) or determine (e.g., based on sensor data) current data such as ward beds status (e.g., the number of occupied/unoccupied beds), intensive care unit status, the locations of doctors, surgeons, nurses and other staff, and pre-operation, operation and post operation equipment location and status. The requirements data 604 received or accessed by the cognitive system 606 can include restrictions or constraints to be applied by the cognitive system 606 when generating a procedural plan. For example, in the context of a procedural plan for performing a surgery, the restrictions can include one or more of: the number of patients should not exceed the number of available beds in the ward, surgeons and other staff required for a procedure should be available at the time of a scheduled procedure, equipment for pre-operation, operation and post operations should be available for the procedure, clinically patients should be treated in a specified amount of time based on the procedure and/or condition, hospital targets should be met or optimized, and surgeon preference should be considered by the system. Based on the facility data and the requirements data, the cognitive system 606 can utilize a demand prediction module 608 to predict demand of the available resources and a procedural plan generation module 610 to generate a procedural plan (e.g., plan for surgery) and any associated recommendations. For example, a procedural plan for a surgery may include one or more of the times, dates, doctors, support staff, equipment, rooms, supplies, beds, and timeframes needed to carry out a surgery, based on the facility data, requirements data and predicted demand. As will be appreciated by those of skill in the art, in various embodiments of the invention, the cognitive system 606 may utilize various algorithms and tools such as machine learning, neural networks, natural language processing, control theory, optimization and other applicable techniques to, for example, predict demand and generate a procedural plan. According to some embodiments, demand prediction module 608 may utilize statistical modelling and supervised machine learning to predict demand and procedural plan generation module 610 may utilize optimization and operations research techniques (e.g., MIP) to generate a procedural plan.

The cognitive system 606 can also include a procedural plan visualization module 612 that can generate a visualization of the procedural plan in a manner similar to that described previous above. The visualization can be displayed by an augmented reality device 614. As will be understood by those of skill in the art, the augmented reality device 612 may provide video, image, sound and/or location data to the procedural plan visualization module 612, which the procedural plan visualization module 612 may use to generate the visualization of the procedural plan (e.g., by determining what content derived from the procedural plan to overlay over which portions of the field of view of the user). For example, the visualization may include one or more ghost images that can be displayed by the augmented reality device 614 (e.g., user device 420) that a user can follow to perform the steps needed to carry about the procedure. According to some embodiments of the invention, a user can manually make modifications to the procedural plan by entering changes to various aspects or variables of the plan. For example, a user could substitute in a different employee in for a suggested or scheduled employee, change a room or piece of equipment scheduled for use in a procedure, change the order of the steps of a procedure or any other such similar changes. Upon making such changes, the system (e.g., augmented reality device 614) may display aspects of the altered procedural plan. According to some embodiments, the system may display a comparison of the original procedural plan versus the altered procedural plan by for example, simultaneously displaying a virtual execution of each plan in virtual or augmented reality. While viewing a virtual execution of a procedural plan, the system may be configured to receive user inputs to make changes or other adjustments to a procedural plan.

The various components, modules, engines, etc. described regarding FIG. 6 can be implemented as instructions stored on a computer-readable storage medium, as hardware modules, as special-purpose hardware (e.g., application specific hardware, application specific integrated circuits (ASICs), application specific special processors (ASSPs), field programmable gate arrays (FPGAs), as embedded controllers, hardwired circuitry, etc.), or as some combination or combinations of these. According to aspects of the present disclosure, the engine(s) described herein can be a combination of hardware and programming. The programming can be processor executable instructions stored on a tangible memory, and the hardware can include the processing device 411 for executing those instructions. Thus a system memory (e.g., memory 412) can store program instructions that when executed by the processing device 411 implement the engines described herein. Other engines can also be utilized to include other features and functionality described in other examples herein.

Figure 7:
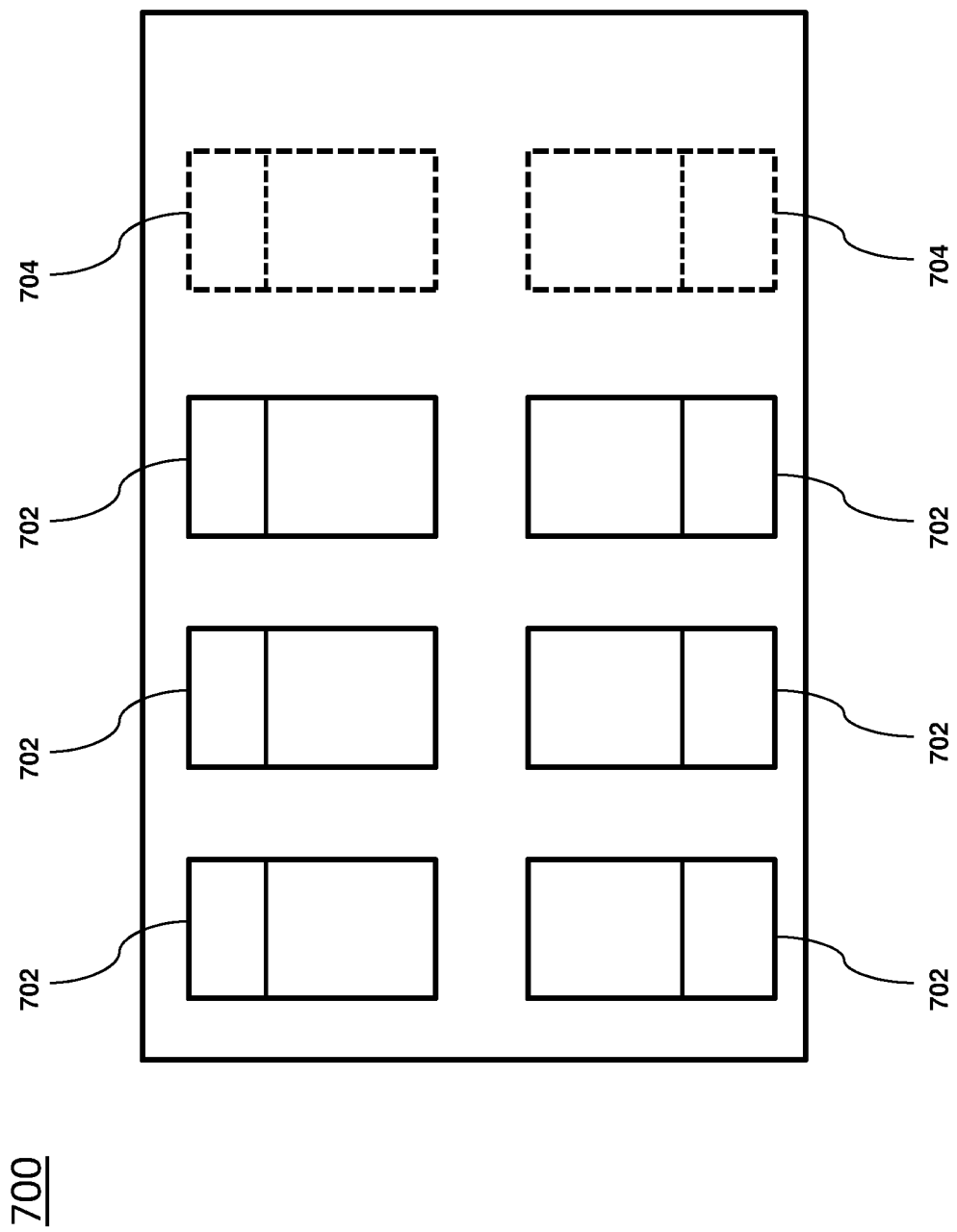
FIG. 7 depicts a visual representation of a portion of a facility rendered by a system for providing an interactive resource plan visualization associated with a facility that illustrates image renderings presented in accordance with first and a second visual styles according to one or more embodiments of the invention.

As previously described above, various embodiments of the invention may include display of some images according to a first visual style and some images according to a second visual style. For example, in some embodiments, available resources can be shown as "solid" images whereas recommended resources can be showing a transparent or semi-transparent images (i.e., "ghost images"). This concept is illustrated by FIG. 7, which shows a display of an aerial view of a room 700 having several available beds 702 along with a display of two recommended beds 704 that may be presented as a recommendation as part of a resource plan as described above. Although this is a simple two-dimensional view, it should be understood that embodiments of the invention contemplate three-dimensional views that can be presented in for example, virtual reality or augmented reality. In the case of augmented reality, available resources may simply be shown as they are in reality, whereas recommend resources may be superimposed as ghost images over a user's view by a user device 420. Likewise, as described previously, an augmented reality device can display ghost images that represent an optimal path or one or more of a sequence of steps to be followed by a wearer of the augmented reality device. Although the first and second visual styles are generally described herein as being solid and semi-transparent, it should be understood that they are not so limited and any type or combination of visual styles may be used to indicate and available resource, a recommended resource or a suggested procedural path to follow, such as for example, applying an artificial/virtual color to an object, presenting an object as a flashing object, providing an annotation next to an object, enhancing the brightness of an object within an image or any other way of making a particular object or image within a user's field of view stand out.

Additional processes may also be included. It should be understood that the processes depicted in FIGS. 5 and 6 represent illustrations, and that other processes may be added or existing processes may be removed, modified, or rearranged without departing from the scope and spirit of the present disclosure.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for visual representation of a facility on a display device, the computer-implemented method comprising:
   receiving, by a processor, facility data comprising historical facility data and current facility data;
   receiving demand data, the demand data including social media data;
   determining, based on the facility data and the demand data and using cognitive computing techniques, projected resource demand;
   generating the visual representation of the facility on the display device, the visual representation of the facility comprising available resources and resource demand associated with a specified time, wherein the available resources are rendered according to a first visual style;
   determining resource availability modifications based on the available resources and the projected resource demand; and
   generating, within the visual representation of the facility on the display device, a visual representation of the resource availability modifications associated with the specified time, wherein the resource availability modifications define suggested changes to modify the available resources and the suggested changes to modify the available resources are rendered for display according to a second visual style within the visual representation of the facility, wherein the processor is configured to use virtual reality or augmented reality to generate the suggested changes of the available resources for display within the visual representation of the facility, the virtual reality or the augmented reality being generated using a three-dimensional representation, wherein the processor is configured to display wards within the visual representation of the facility using a symbolic representation indicative of which ones of the wards meet a threshold, the symbolic representation further indicative of virtual content configurable by a user, wherein the visual representation of the facility comprises the three-dimensional representation of the facility for display and manipulation by a computing device, and wherein a view of the three-dimensional representation is configured to be modified by the user of the computing device to view different portions of the three-dimensional representation of the facility.

2. The computer-implemented method of claim 1, wherein the facility data comprises data representative of the available resources and resource demand.

3. The computer-implemented method of claim 2, wherein the available resources comprise at least one of operation rooms, surgical equipment, doctors, nurses, medication and medical supplies.

4. The computer-implemented method of claim 1, wherein the demand data further comprises weather data.

5. The computer-implemented method of claim 4, wherein deployed ambulance data comprises a GPS location and a patient diagnosis of one or more deployed ambulances.

6. The computer-implemented method of claim 1, wherein the projected resource demand comprises the predicted demand for the available resources in relation to one or more a future time periods.

7. The computer-implemented method of claim 1, wherein determining the projected resource demand using cognitive computing techniques comprises using one or more of statistical models and supervised machine learning to predict future demand based on the historical facility data and current facility data.

8. The computer-implemented method of claim 1, wherein the first visual style comprises an opaque image, whereas the second visual style comprises a semi-transparent image.

9. The computer-implemented method of claim 1, further comprising:
   receiving a user input indicative of a different specified time; and
   modifying at least one of the visual representation of the available resources, resource demand and resource availability modifications to represent data associated with the different specified time.

10. The computer-implemented method of claim 1, wherein the processor is configured to communicate with one or more sensors positioned within the facility to generate the visual representation of the facility, the one or more sensors further being used to determine the demand data and the projected resource demand, the one or more sensors including a camera, a microphone, a scanner, an infrared camera, and a light detection and ranging (LiDAR) sensor.

11. The computer-implemented method of claim 1, wherein:
the processor is configured to use one or more sensors to make real-time observation of a medical procedure; and
in response to the real-time observation, the processor is configured to cause modifications to a procedural plan for the medical procedure such that the procedural plan comprises a visualization of virtual execution according to the modifications.

12. The computer-implemented method of claim 1, wherein the facility data comprises staff and patients, the processor being configured to distinguish between the staff and the patients based at least in part on badges, logos, clothing, and associated equipment.

13. The computer-implemented method of claim 1, wherein the social media data is related to a health problem.

14. A system for visual representation of a facility on a display device, the system comprising:
a processor communicatively coupled to a memory, the processor configured to:
receive facility data comprising historical facility data and current facility data;
receive demand data, the demand data including social media data;
determine, based on the facility data and the demand data and using cognitive computing techniques, projected resource demand;
generate the visual representation of the facility on the display device, the visual representation of the facility comprising available resources and resource demand associated with a specified time, wherein the available resources are rendered according to a first visual style;
determine resource availability modifications based on the available resources and the projected resource demand; and
generate, within the visual representation of the facility on the display device, a visual representation of the resource availability modifications associated with the specified time, wherein the resource availability modifications define suggested changes to modify the available resources and the suggested changes to modify the available resources are rendered for display according to a second visual style within the visual representation of the facility, wherein the processor is configured to use virtual reality or augmented reality to generate the suggested changes of the available resources for display within the visual representation of the facility, the virtual reality or the augmented reality being generated using a three-dimensional representation, wherein the processor is configured to display wards within the visual representation of the facility using a symbolic representation indicative of which ones of the wards meet a threshold, the symbolic representation further indicative of virtual content configurable by a user, wherein the visual representation of the facility comprises the three-dimensional representation of the facility for display and manipulation by a computing device, and wherein a view of the three-dimensional representation is configured to be modified by the user of the computing device to view different portions of the three-dimensional representation of the facility.

15. The system of claim 14, wherein the facility data comprises data representative of the available resources and resource demand.

16. The system of claim 15, wherein the available resources comprise at least one of operation rooms, surgical equipment, doctors, nurses, medication and medical supplies.

17. The system of claim 14, wherein the first visual style comprises an opaque image, whereas the second visual style comprises a semi-transparent image.

18. A computer program product for visual representation of a facility on a display device, the computer program product comprising a computer readable storage medium having program instructions embodied therewith the program instructions executable by a processor to cause the processor to perform a method comprising:
receiving facility data comprising historical facility data and current facility data;
receiving demand data, the demand data including social media data;
determining, based on the facility data and the demand data and using cognitive computing techniques, projected resource demand;
generating the visual representation of the facility on the display device, the visual representation of the facility comprising available resources and resource demand associated with a specified time, wherein the available resources are rendered according to a first visual style;
determining resource availability modifications based on the available resources and the projected resource demand; and
generating, within the visual representation of the facility on the display device, a visual representation of the resource availability modifications associated with the specified time, wherein the resource availability modifications define suggested changes to modify the available resources and the suggested changes to modify the available resources are rendered for display according to a second visual style within the visual representation of the facility, wherein the processor is configured to use virtual reality or augmented reality to generate the suggested changes of the available resources for display within the visual representation of the facility, the virtual reality or the augmented reality being generated using a three-dimensional representation, wherein the processor is configured to display wards within the visual representation of the facility using a symbolic representation indicative of which ones of the wards meet a threshold, the symbolic representation further indicative of virtual content configurable by a user, wherein the visual representation of the facility comprises the three-dimensional representation of the facility for display and manipulation by a computing device, and wherein a view of the three-dimensional representation is configured to be modified by the user of the computing device to view different portions of the three-dimensional representation of the facility.

19. The computer program product of claim 18, wherein:
the visual representation of the facility comprises the three-dimensional representation of the facility for display and manipulation by a computing device; and
a view of the three-dimensional representation is configured to be modified by a user of the computing device to view different portions of the three-dimensional representation of the facility.

* * * * *